United States Patent [19]

Manchak, Jr.

[11] Patent Number: 4,834,194
[45] Date of Patent: May 30, 1989

[54] METHOD AND APPARATUS FOR DETECTION OF VOLATILE SOIL CONTAMINANTS IN SITU

[76] Inventor: Frank Manchak, Jr., 11300 S. Norwalk Blvd., Santa Fe Springs, Calif. 90670

[21] Appl. No.: 120,025

[22] Filed: Nov. 13, 1987

[51] Int. Cl.[4] .................... E21B 49/00; E21B 47/086
[52] U.S. Cl. .................................... 175/50; 175/17; 175/59; 175/325; 175/393; 166/250; 166/265; 166/290; 366/102; 366/140; 366/147; 366/348; 405/128; 405/263; 405/266; 405/131
[58] Field of Search ................... 73/19, 863.11, 863.12, 73/864.43; 55/61, 198; 210/747, 170; 405/131, 258, 269, 263, 266, 270, 131, 128, 129; 166/369, 370, 265, 264, 250; 175/50, 58, 59, 17, 60, 24, 26, 325, 393; 366/65, 102, 105, 140, 144, 147, 279, 289, 320, 347, 348

[56] References Cited

U.S. PATENT DOCUMENTS

| | | | |
|---|---|---|---|
| 2,141,261 | 12/1938 | Clark | 175/19 |
| 3,084,553 | 4/1963 | Cullinan et al. | 175/21 |
| 3,968,845 | 7/1976 | Chaffin | 175/60 |
| 4,189,184 | 2/1980 | Green | 166/265 X |
| 4,249,828 | 2/1981 | Condolios | 366/102 |
| 4,315,757 | 2/1982 | Woodmansee | 266/147 |
| 4,323,122 | 4/1982 | Knopik | 166/369 X |
| 4,332,301 | 6/1982 | Jonell | 175/50 |
| 4,341,273 | 7/1982 | Walker et al. | 175/393 X |
| 4,385,669 | 5/1983 | Knutsen | 175/325 X |
| 4,469,176 | 9/1984 | Zison et al. | 166/369 X |
| 4,593,760 | 6/1986 | Visser et al. | 166/370 X |
| 4,670,148 | 6/1987 | Schneider | 73/19 X |
| 4,670,634 | 6/1987 | Bridges et al. | 405/131 X |
| 4,792,237 | 12/1988 | Hara | 175/19 |

Primary Examiner—Bruce M. Kisliuk
Attorney, Agent, or Firm—Roth & Goldman

[57] ABSTRACT

The invention relates to methods and apparatus for agitating and heating a sub-surface volume of soil to liberate volatile compositions therefrom which are transmitted through a special flow passage created through the soil to the soil surface where they are analysed to determine the presence or absence of selected contaminants. A low pressure sink is provided to ensure proper flow of volatiles rapidly to the surface and to prevent contamination of adjacent soil blocks or cylinders during treatment.

20 Claims, 6 Drawing Sheets

METHOD AND APPARATUS FOR DETECTION OF VOLATILE SOIL CONTAMINANTS IN SITU

CROSS REFERENCES TO RELATED APPLICATIONS

My co-pending U.S. applications Ser. No. 865,745, filed Aug. 26, 1985 now U.S. Pat. No. 4,776,409, for In Situ Waste Impoundment Treating Apparatus and Method of Using Same and Ser. No. 049,861 each disclose apparatus which physically agitates a subsurface volume of soil in situ, and preferably injects a heated fluid such as steam into the agitating soil which then releases volatile components which percolate upwardly through the soil to the ground surface where they can be analysed. Treatment methods and chemicals are then selected depending on the composition of the volatile components liberated from the sub-surface soil.

My co-pending U.S. patent application Ser. No. 093,305 filed Sept. 3, 1987 for a Device for Sampling Soils and Retaining Volatiles Therein and Method of Using Same discloses a soil sampling device which is inserted into the ground for taking an undisturbed soil sample and removing it from its subterranean location without loss of volatile components from the soil sample.

BACKGROUND OF THE INVENTION AND PRIOR ART

Although the inventions disclosed in my prior pending applications mentioned above perform perfectly well for their intended purposes, the apparatus shown in Ser. Nos. 865,745 and 049,861 is designed not only for the purpose of analysing the composition of soil contaminants but also for treating the soil, if necessary. In general, this results in apparatus which is larger and slower than need be for preliminary site testing where it is desirable to provide analytical results in real time.

The inventions disclosed in Ser. No. 093,305 are intended for site analysis by gathering physically undisturbed samples of soil rather than for making a real time analysis of the contaminant content by liberating volatiles from the soil which are then analysed at the surface.

Accordingly, it is an object of the present invention to provide an improved method and apparatus for liberating volatile gases from sub-surface soil locations which more quickly conducts the volatiles to the surface to enable analysis of such gases to determine the soil contents in real time. An additional object of the invention is to provide improved treatment methods and apparatus designed to ensure that no contamination of adjacent soil blocks takes place during treatment of the currently treated block or blocks.

SUMMARY OF THE INVENTION

The present invention accordingly provides a method of analysing soil to determine contaminants therein wherein a block or cylinder of soil is agitated and heated to release volatile contaminants which are then conducted through a relatively unobstructed flow path created in the soil to the surface where they may be analysed. Two different embodiments of apparatus for performing the method are disclosed.

DESCRIPTION OF THE PREFERRED EMBODIMENT

Figure 1:
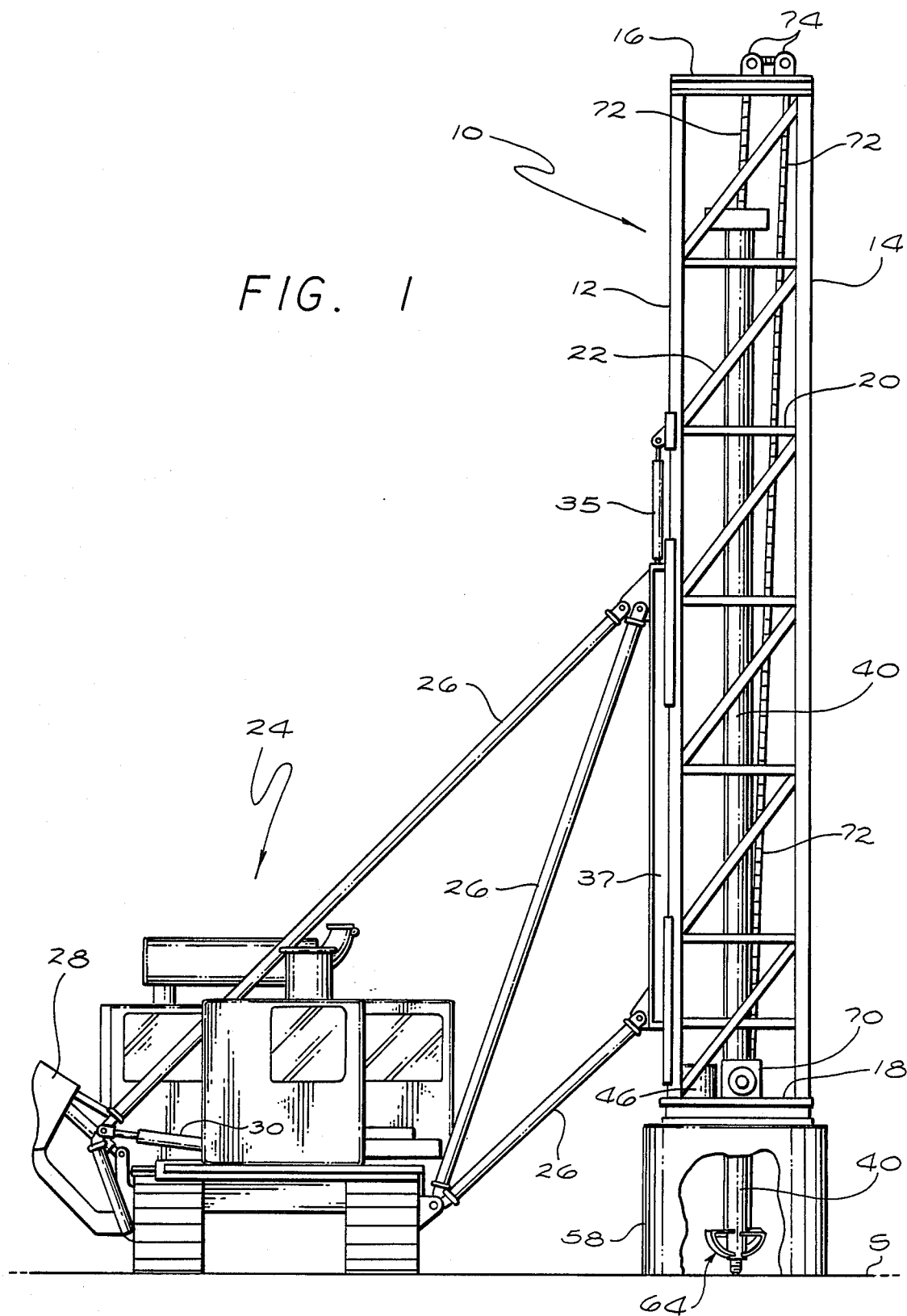
FIG. 1 is an elevational view of the present invention shown mounted on a mobile tractor rig.

FIG. 1 shows a vertically extending main frame 10 comprised of four corner members 12, 14 extending vertically between an upper platform 16 and a lower platform 18. The corner members 12, 14 are connected together by a plurality of cross pieces 20 and diagonal reinforcing members 22 to provide structural rigidity.

The main frame 10 is connected to a mobile tractor rig 24 by a plurality of struts 26 which are pivotally connected at one end to a lifting frame 37 and at the other end to the tractor rig 24 as shown. A counterweight 28 and hydraulic piston unit 30 on the tractor rig 24 permit lateral positioning of the main frame 10 relative to the tractor as desired. A vertical lifting piston/cylinder unit 35 connected at one end to the main frame 10 and at the other end to the lifting frame 35 is used to raise and lower the apparatus during movement from one location to the next.

Mounted within the frame 10 is a vertically extending stem or rotatable Kelly 40 driven for rotary movement by a motor 46 shown on the lower platform 18. A geared connection between the motor 46 and a rotary drive table 48 which surrounds the Kelly 40 imparts rotary movement thereto. A motor load monitor is also provided for the purpose of obtaining motor load data which is representative of the plasticity of the soil being worked. The plasticity data is then used by the operator to adjust the speed of rotation of the Kelly 40 as necessary. Guide rollers 60 mounted on the table 48 engage vertically extending splines 50 on the Kelly 40 to guide vertical movement thereof. The mounting and the drive arrangement for the Kelly 40 are shown herein schematically as the detailed construction is well known in the prior art as, for example, in my prior application Ser. No. 049,861 mentioned above.

A rigid gas containment shroud 58 is affixed to the underside of lower platform 18 at the lower end of the frame 10 and is positioned such that its lower edge 59 sealingly engages the earth surface S during operation of the device so as to prevent gases escaping from the block or cylinder of soil being worked from contaminating the ambient atmosphere. A rotary cutter 64 having a pair of oppositely disposed horizontally extending cutter blades 65 is affixed to the lower end of the Kelly 40. Powered drive means including a motor 70 and chain 72 trained over pulleys 74 is provided for vertical movement of the Kelly 40 and attached cutter 64 as is well known in the art.

Figure 2:
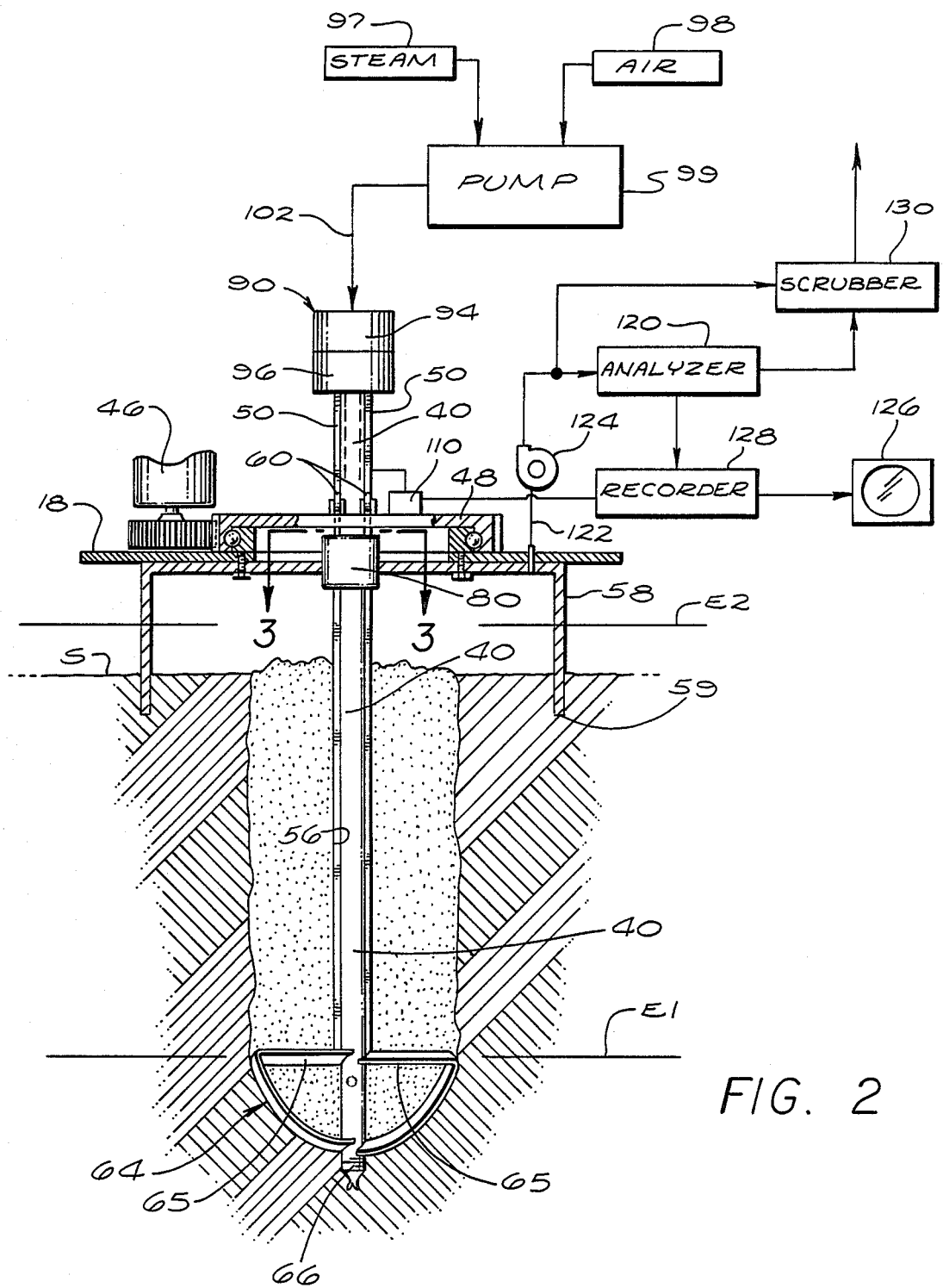
FIG. 2 is a sectional elevation view of a first embodiment of the present invention showing a single rotary cutter-injector.

Turning now to FIG. 2, a schematic view of a first and presently preferred embodiment of the invention is shown in which a vertically extending hollow Kelly 40 is provided with at least one longitudinally extending spline 50 or annulus cutter welded to the exterior thereof. The spline or splines 50 preferably continuously extends along the vertical length of the Kelly 40 from the elevation of the cutter 64 at the bottom upwardly to the soil surface S and thence through a rotary gas seal 80 in the shroud 58, then through the lower platform 18 and Kelly drive table 48 and finally upwardly to a swivel 90 attached to the upper end of the Kelly 40 for vertical movement therewith for a purpose to be described. The spline 50, during rotation of the Kelly 40, continuously cuts and keeps open, an annular passageway 56 which extends vertically from a first elevation E1 at the cutter blades 65 upwardly to a second elevation E2 from which gas is withdrawn from the annulus 56. Preferably gas is withdrawn from the annulus 56 at the elevation of the shroud 58; however, it is possible to withdraw the gas from a different elevation than the elevation of the shroud.

The swivel 90 is for the purpose of introducing pressurized fluid which may comprise steam or hot air from sources 97, 98 thereof into the rotating Kelly 40 through which it can be conducted downwardly for discharge at the cutter 64. A pressure intensifier pump 99 is provided as shown. The swivel 90 has a non-rotatable upper portion 94 and a lower rotatable portion 96 affixed to the Kelly 40 for rotation therewith. Both portions of the swivel 90 move vertically with the Kelly 40 as it is raised and lowered into operative positions for cutting at different elevations. The source of high pressure fluid connected by a flexible hose 102 to the upper swivel portion 94 in fluid communication with the interior of the hollow Kelly 40 or, alternatively, into a separate conduit (not shown) which may be provided in the Kelly 40. Typically, a separate conduit inside the Kelly will be chosen if it is desired to eject steam from the cutter 64 into the soil whereas if only hot air is to be ejected, the interior of the Kelly 40 can be used as the air flow passageway and a separate conduit is not needed.

Figure 3A:
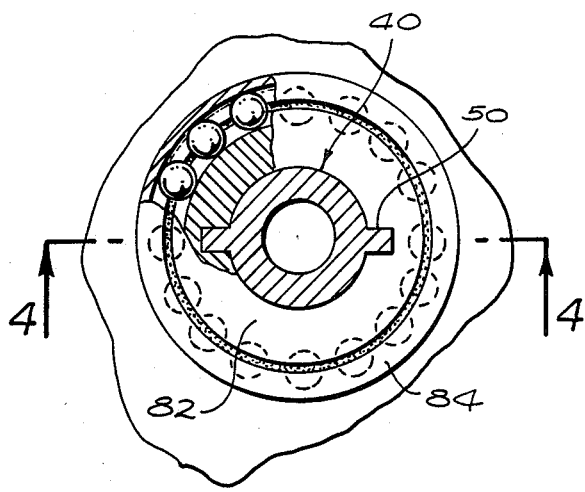
FIG. 3A is a horizontal section taken at line 3—3 of FIG. 2.
Figure 3B:
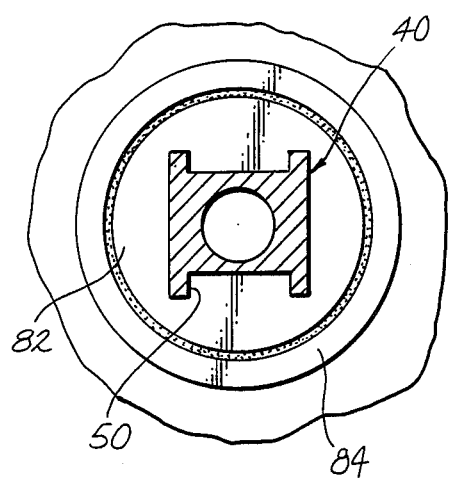
FIG. 3B is a horizontal section like FIG. 3A but showing an alternative cross sectional shape of the Kelly.

FIGS. 3 A and 3 B show alternative cross sectional configurations of the Kelly 40. In either instance at least one longitudinally extending radial protrusion or spline 50 is needed to cut the annulus 56 during rotation of the Kelly 40.

Figure 5:
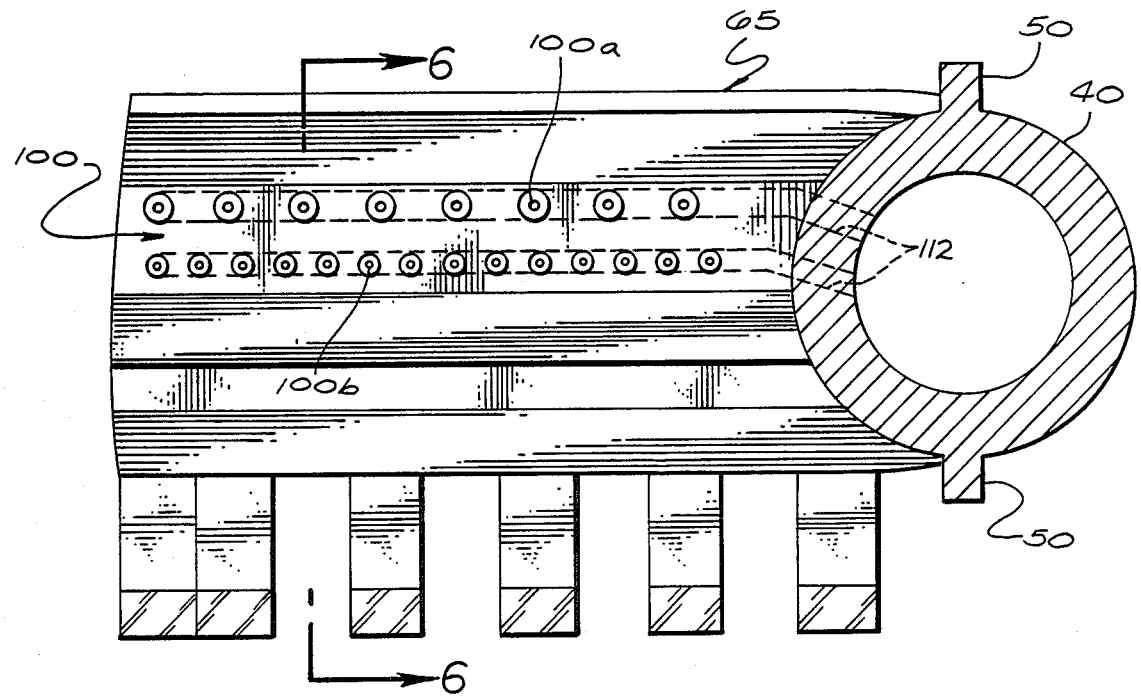
FIG. 5 is a plan view to an enlarged scale of one of the cutter blades used in a first embodiment of the invention.
Figure 6:
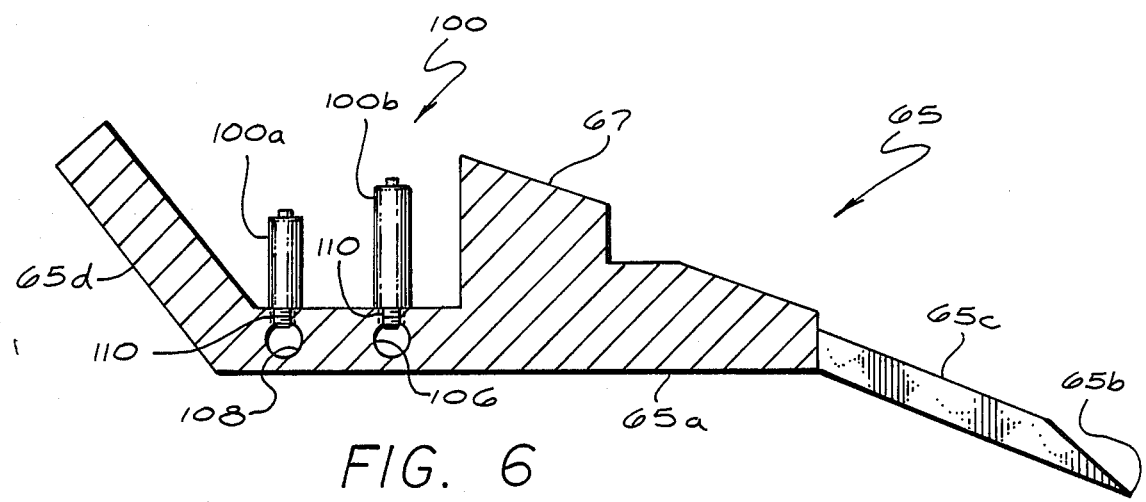
FIG. 6 is a vertical cross section taken at line 6—6 of FIG. 5.

A pilot bit 66 may be affixed to the lower end of the Kelly 40. Cutter blades 65 as best seen in FIGS. 5 and 6 are affixed to the lower end of the hollow Kelly 40 and the Kelly interior (or the conduit therein if present) is placed into fluid communication with fluid passageways 106, 108 in the cutter blades 65 and fluid discharge jets 100 in fluid communication with the passageways 106, 108.

High pressure fluid from the sources 97, 98 is jetted outwardly from a plurality of jets 100 provided in the cutter 64 for this purpose. The heated fluid volatilizes many of the contaminant components typically found in waste disposal sites and causes them to migrate upwardly to the ground surface where they are collected in the shroud 58.

A vertical travel monitor 110 is provided on the lower platform 18 for the purpose of accurately recording the vertical position of the Kelly 40 and, hence the first elevation or depth of the cutter 64 below a reference datum plane. This position data is then sent to a central processing unit for correlation with data provided by a gas analyser 120 which receives gas from the shroud 58 via a conduit 122 and a blower 124 for determining the composition of the gas collected in the shroud 58. The gas analyser typically comprises one or more of a flame ionization detector (FID), a gas chromatograph, a radiation detector, reactivity and conductivity analysers, a biological analyser, pH and oxidation reduction potential (ORP) meters, temperature and moisture meters and other components well known in the art. As described below, depth data can be correlated with gas contaminant composition and concentration data with sufficient precision to provide an accurate profile of the soil contaminants, their concentration and the depth at which the contaminants were encountered. Two or three dimensional maps of the contaminated ground area can then be made to display the correlated data. A monitor 126 for visual observance and a strip chart recorder 128 which provides a paper printout of the data in real time are provided so that the operator may then, if desired, repeat the process for verification. The blower 124 maintains a sufficiently negative pressure in the shroud 58 so that gases therein are not transmitted to atmosphere before passing through a gas scrubber 130 which removes harmful contaminants therefrom.

Figure 4:
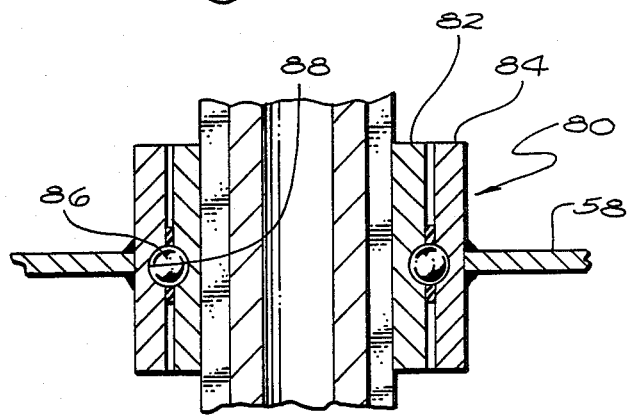
FIG. 4 is a vertical section on an enlarged scale of the Kelly seal shown in FIG. 2.

A vertical cross section of the gas seal 80 in the shroud 58 is shown in FIG. 4 to comprise an inner, rotatable section 82 affixed to the Kelly 40 for rotation therewith and a stationary outer section 84 mounted in the top wall of the shroud 58. Bearings 86 mounted in a packed multi-part race 88 provide minimum friction between the relatively rotating parts 82, 84.

The cutter assembly is affixed to the lower end of the Kelly 40 and may be provided with a pilot bit 66 as shown.

Figure 7:
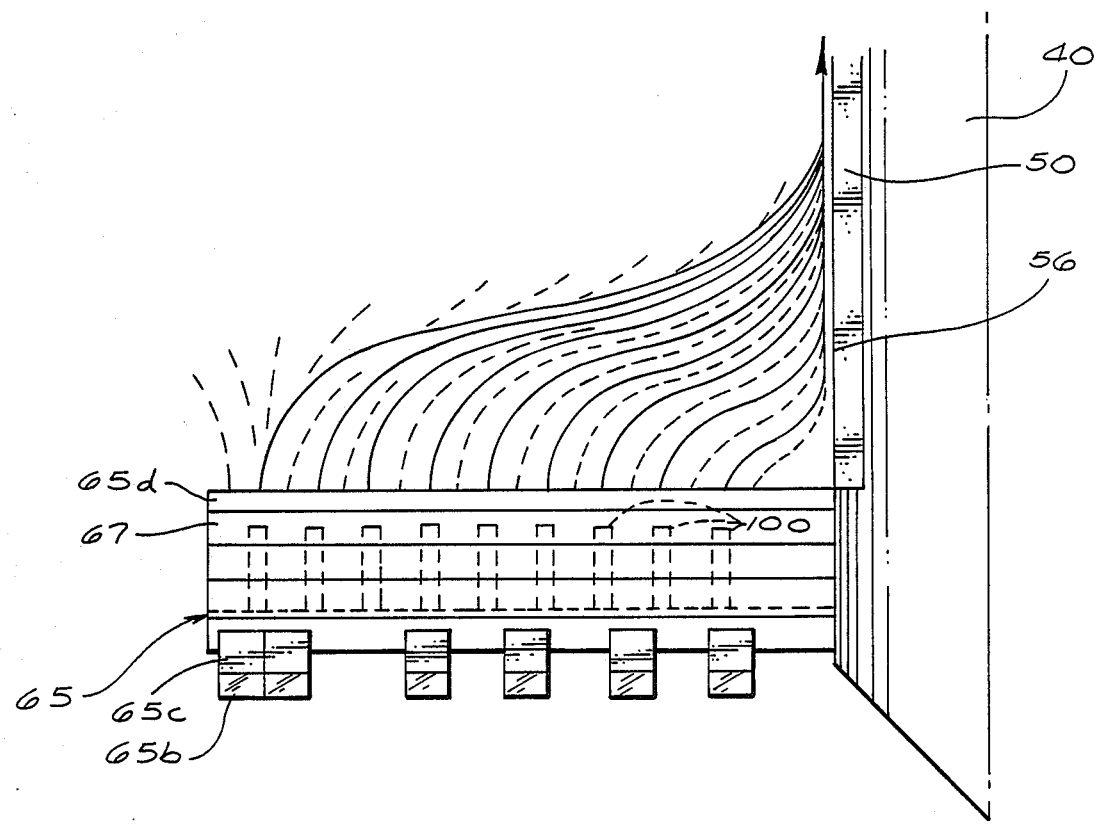
FIG. 7 is a view, similar to FIG. 5, showing the pattern of gas flow in the region of the cutter.

FIGS. 5, 6 and 7 show a presently preferred radial blade cutter design and the manner in which the cutter blades 65 create a zone of influence, i.e. a zone in which volatilization of contaminants takes place due to the combined action of agitation of the soil by the cutter blades 65 and the heating thereof by the high pressure fluid injection. Momentary heating of the soil in the zone of influence is coupled with physical agitation and homogenization of the soil near the cutters resulting in volatilization of contaminants in the soil. The cutter blades 65, together with the annulus cutter 50, open a substantially unobstructed flow path to rapidly conduct gases directly from the cutters to the shroud 58 where they can be analysed and correlated with the depth from which they originated. The blower 124 keeps the shroud 58 under a negative pressure, preferably minus about 4 inches of water, which creates a low pressure sink to which the volatile contaminants are directed. The cutter blade 65 has a generally planar horizontal portion 65a which extends radially from the Kelly 40 and which is provided with preferably two separate internal passageways 106,108 for conducting air and/or steam therethrough. It will be appreciated that a single passageway can be provided instead of two separate passageways but that certain contaminant conditions encountered may make the use of air preferable to the use of steam (as for example when the ground water table is high or the soil is saturated) or vice versa. Thus, increased flexibility is afforded when separate passageways for air and steam are provided. As shown, the leading edge 65b of the cutter is provided with a plurality of spaced, downwardly inclined teeth 65c for cutting into the soil. Intermediate the leading and trailing edges 65b, 65d of the cutter an upstanding shield 67 is provided to protect the upwardly extending air and steam jets 100a, 100b during the cutting operation. The steam jets 100b are provided in a row behind the shield 67 and the air jets 100a are provided in a row behind the steam jets 100b. This positioning of the air jets behind the steam jets asssists in keeping an open flow path from the cutters to the annulus 56 when both steam and air are used. The jets 100 may, if desired be angled toward the Kelly 40 to assist in formation of the desired flow path. Finally, the cutter blade 65 is provided with an upwardly inclined trailing edge 65d as shown. The trailing edge 65d creates a radially extending flow path which is relatively unobstructed behind the cutter blade 65 from the jets 100 to the annulus 56 and the upward inclination of the trailing edge 65d assists in withdrawing the cutter 64 from the soil when the direction of rotation of the Kelly 40 is reversed.

Internally, each cutter blade 65 is provided with a pair of through bores 106, 108 which in turn are intersected by vertical bores 110 into which individual jet nozzles 100 are threadedly connected. The through bores 106, 108 terminate at the Kelly 40 which has been provided with a pair of fluid discharge ports 112 extending through the lower end of the Kelly wall so that high pressure fluid from the Kelly interior (or from a separate conduit if desired) is communicated to the jet nozzles 100.

The speed of rotation of the Kelly 40 is continuously monitored and is increased with increasing moisture content of the soil as determined by a moisture content sensor so as to maintain the annular passageway 56 unobstructed. It has been found that high water content in the soil has the effect of more rapidly clogging up the passageway 56. Rotation rates typically very from 5 RPM to 30 RPM with typical speeds for contaminant analysis comprising about 20–25 RPM and slower speeds being used for treatment of contaminated soil by repeated stripping or injection of treatment chemicals. Reversal of the direction of rotation when withdrawing the cutters 64 from the soil results in re-compaction of the soil to its initial condition. Also, higher speeds of rotation generally result in the intended volatilization of larger proportions of volatile contaminants.

FIG. 7 shows the path of flow of the fluid ejected from the jets 100 first radially inwardly toward the Kelly 40 through the path created behind the trailing edge 65d of the cutter blade 65 and thence upwardly in the annulus 56 surrounding the Kelly 40 to the underside of the shroud 58 which is maintained under negative pressure. Although the embodiment of the apparatus shown in FIG. 2 creates an annular flow passageway, it will be appreciated that, in its broadest aspects, the passageway need not be annular in cross section. For example, an I beam can be used instead of a round Kelly and the flow passageway created by rotation of the I beam would comprise the essentially rectangular cross section areas between the flanges and web of the I beam.

Although the present invention is concerned primarily with methods and apparatus for obtaining data concerning soil contamination, when contaminants are found, treatment may be dictated. This treatment may consist of any combination of steps including the injection of additional hot air or steam for stripping of volatile contaminants, injection of treatment chemicals or biological treatment media, etc. Pressures of up to 5000 psi are typically used with fluids at temperatures usually exceeding 50° C. to liberate volatile contaminants. Concern has been expressed that such high pressures may result in the recontamination of soil in the block or cylinder of soil above the cutter or in the contamination of previously cut adjacent cylinders.

Figure 8:
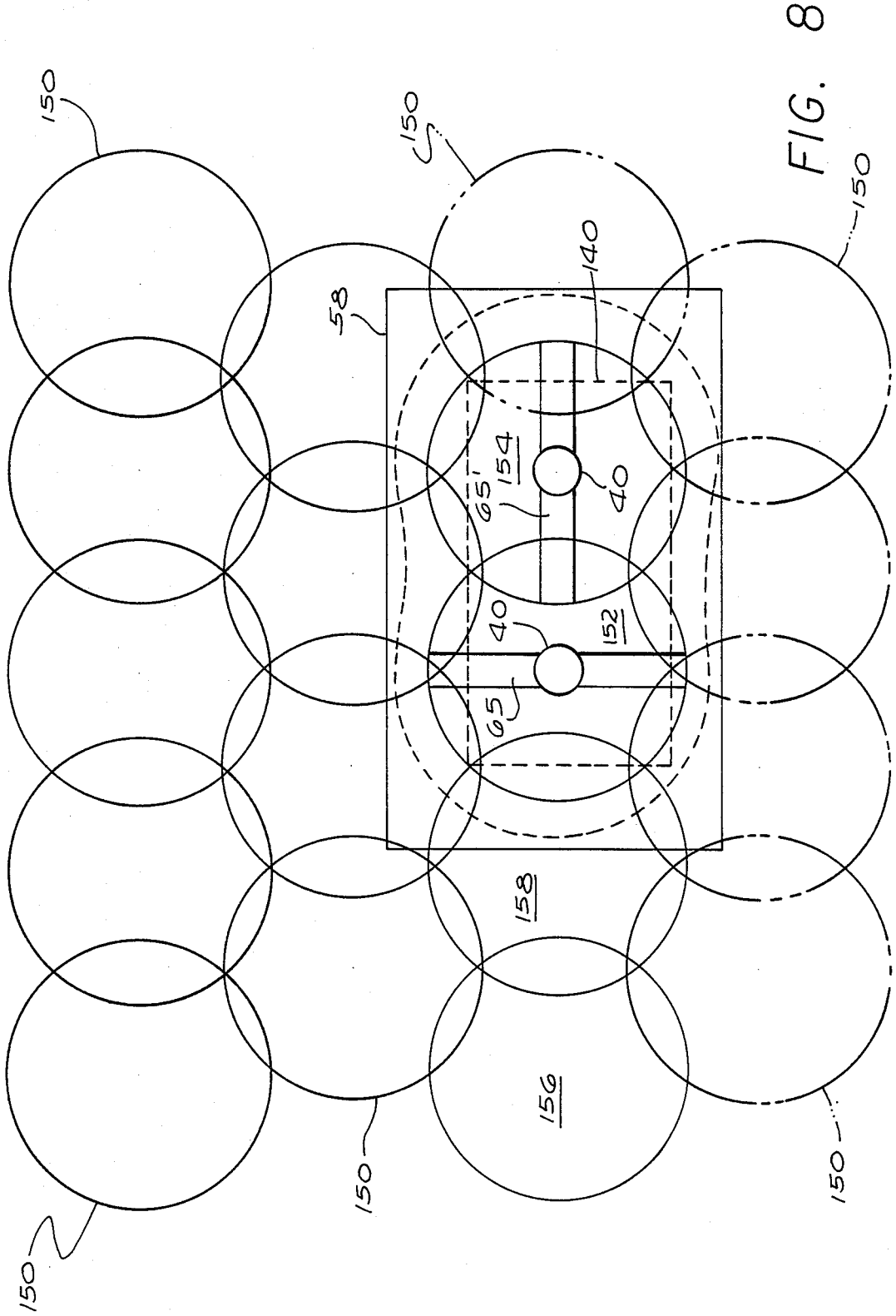
FIG. 8 is a plan view showing the pattern of treatment of soil blocks with a multiple rotary cutter treatment apparatus in a waste impoundment.

FIG. 8 shows a plan view of the pattern of treatment of a contaminated soil area using a pair of overlapping counter rotating cutter injectors 65, 65' enclosed in a single rectangular shroud 58. The frame 10, shroud 58, Kelly or Kelleys 40 and the cutter or cutters 65, 65' are moved as a unit from one location to the next during soil analysis and treatment. As seen, the zones 140 overlap and the apparatus is positioned such that there is overlap between the boundaries 150 of the cylinders to be treated so that there are no untreated areas. The low pressure sink and flow path for volatile contaminants created by the present design ensures that the high pressures employed do not overpressurize the cylinders of soil being worked 152, 154 or contaminate adjacent previously treated soil cylinders 156, 158 but instead, the volatile contaminants are immediately communicated to the shroud 58 where they can be analysed and scrubbed to remove contaminants.

By way of example rather than limitation, apparatus intended primarily for contaminant analysis rather than treatment employs a cutter diameter of about 2'0" whereas an apparatus designed for treatment employs a 5'0" dual cutter arrangement wherein each cutter-injector is sized to treat a rectangular block or zone shown within the boundaries in FIG. 8 of 7'4" by about 4'0" or less.

Figure 9:
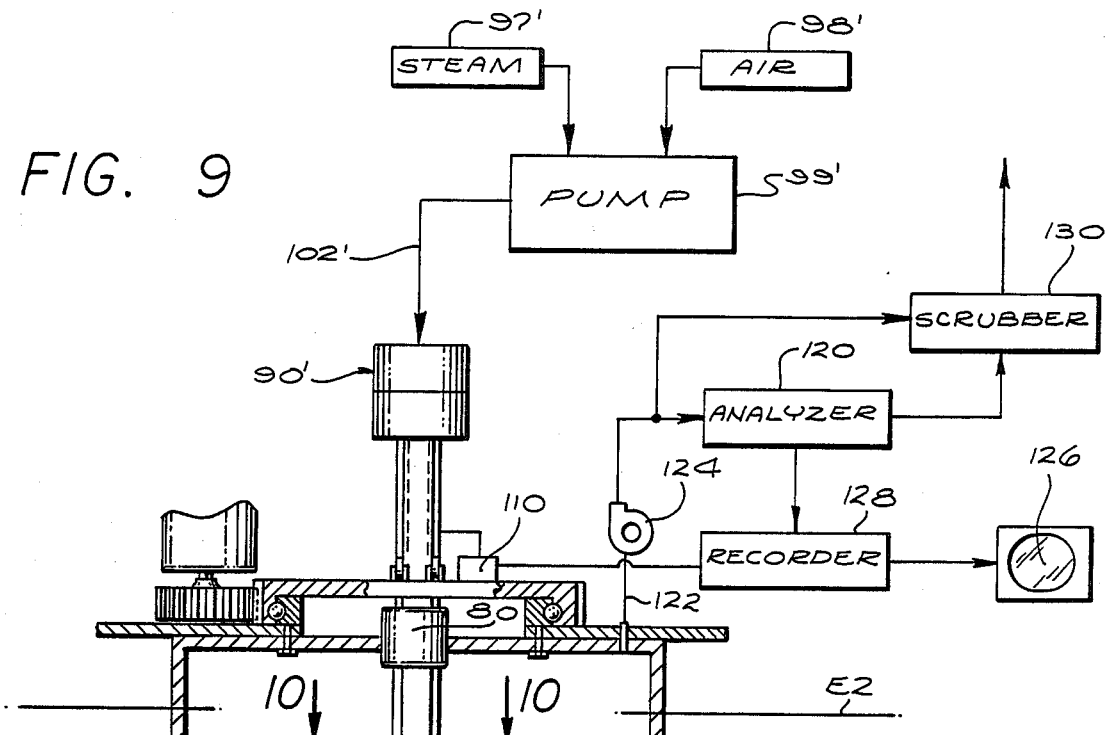
FIG. 9 is a sectional elevation view of a second embodiment of the present invention showing which uses a high pressure jet injector/cutter.
Figure 10:
FIG. 10 is a horizontal cross section taken at line 10—10 of FIG. 9.

FIGS. 9 and 10 show a second embodiment of the invention which employs a Kelly 40 having downwardly extending teeth 159 on the lower end thereof and a plurality of high pressure fluid jet cutters 160 rather than the blade cutters 64 shown in FIGS. 5 and 6. It has been found that fluid jet cutters 160 which employ fluid pressures as high as 30,000 psi are capable of thoroughly cutting and agitating the soil for a sufficiently large radius outwardly from the Kelly 40 that radially extending rigid cutter blades 65 are not required. In the FIG. 9 embodiment, three vertically spaced rows each comprising four equally spaced jets 160 which are directed downwardly and outwardly as shown. Some of the jets 160 may be positioned at the lower end of the Kelly between the teeth 159 such that the rotating cutting teeth 159 shield and protect the lowermost jets 160. The high pressure fluid source 98' may comprise an ultrahigh pressure water pump of the type supplied by Admac Corp. of Kent, Wash. Alternatively, a high pressure air compressor may be utilized. The use of very high pressure has the added benefit of eliminating the need for means to heat the fluid at the surface to a temperature required to volatize the contaminants because the extremely high pressure fluid automatically undergoes a substantial temperature elevation during its forced passage through the nozzles. It is essential that the annulus cutter 50 be sized to cut an annulus 56 of sufficient cross sectional area to conduct all of the extremely high pressure fluid to the surface so as to avoid recontamination of adjacent cylinders caused by the extremely high pressure.

High pressure fluid from the source 98' thereof is conducted to the individual jet cutters 160 by high pressure conduit 102' and a swivel 90' as seen in FIG. 2, the main difference being to ensure that sufficiently high pressure swivels and conduit connections are employed to withstand the higher pressures involved.

Persons skilled in the art will readily appreciate that various modifications can be made from the preferred embodiment thus the scope of protection is intended to be defined only by the limitations of the appended claims.

I claim:

1. Apparatus for liberating volatile contaminants from soil without contaminating the ambient atmosphere comprising:
   (a) cutter means mounted on a rotary stem for agitating a block of soil having an exposed surface in situ;
   (b) means for heating said block of soil at a first elevation therein during said agitation including fluid injection means mounted on said stem for injecting heated fluid into said block of soil at said first elevation;
   (c) means for sealing off said exposed surface of said block to prevent escape to atmosphere of gases or vapors generated during said agitation and heating;
   (d) means for withdrawing said gases or vapors from a second elevation above said first elevation of said block; and
   (e) annulus cutter means mounted on said stem and extending between said first elevation and said second elevation for cutting a continuous passageway extending between said first elevation and said second elevation for conducting said gases and vapors from said first elevation in said block to said means for withdrawing said gases or vapors.

2. The apparatus of claim 1, wherein said annulus cutter comprises at least one radial protrusion on said stem extending between said first and second elevations.

3. The apparatus of claim 2 wherein said radial protrusion is a spline extending longitudinally of said rotary stem.

4. The apparatus of claim 1, wherein said rotary cutter means comprises
   at least one blade extending radially outwardly from said stem at said first elevation, said stem having fluid conduit means therein for conducting fluid from a source thereof to said first elevation, said blade having fluid passageway means therein in fluid communication with said conduit means in said stem, and a plurality of fluid jet nozzles on said blade in fluid communication with said passageway means.

5. The apparatus of claim 1, wherein said cutter means and said means for heating comprise fluid conduit means in said stem for conducting said fluid from a source thereof to said first elevation, and
   a plurality of high pressure jet nozzles mounted on said stem in fluid communication with said conduit means, said nozzles being angled downwardly and radially outwardly from said stem to provide a circular discharge pattern at said first elevation.

6. The apparatus of claim 4 or 5, further comprising monitoring means for producing data indicating the vertical position of said means for agitating relative to a reference datum, means for analysing said withdrawn gases to produce data indicating the composition thereof, and means for correllating the vertical position data with the gas composition data.

7. Method of analyzing soil in situ to determine contaminants therein comprising the steps of:
   (a) agitating a block of soil in situ;
   (b) injecting heated fluid into said block of soil during agitation thereof to liberate volatile contaminants at a first elevation therein;
   (c) continuously, during said agitation, creating a passageway for gases or vapors in said block of soil, said passageway extending from said first elevation to a second elevation thereabove;
   (d) withdrawing gases or vapors from said block of soil at said second elevation above said first elevation; and
   (e) analyzing said withdrawn gases and vapors in real time to determine the composition thereof.

8. The method of claim 7, wherein a rotary cutter performs said agitation step and said heating is by injecting a stream of pressurized heated fluid at the elevation of said cutter and further comprising the step of continuously cutting said passageway with a rotary annulus cutter and exhausting said pressurized fluid through said passageway.

9. The method of claim 8, comprising the step of causing said pressurized heated fluid to flow through a path which extends from radially outer portions of said rotary cutter radially inwardly to an annulus and thence through said annulus from said first elevation to said second elevation.

10. The method of claim 9, wherein said pressurized heated fluid is heated air.

11. The method of claim 9, wherein said pressurized heated fluid is steam.

12. The method of claim 11, further comprising the steps of sensing the moisture content of said agitating soil and increasing the speed of rotation of said cutter as increased moisture content is sensed.

13. The method of claim 9, wherein said heating step comprises the sequential sub-steps of heating with hot air followed by heating with steam.

14. The method of claim 13, wherein contaminated vapors or gases are treated to remove contaminants therefrom following withdrawal of said gases or vapors form said block.

15. The method of claim 14, further comprising the step of injecting chemical oxidants into said soil in situ to neutralize unremoved contaminants therein.

16. The method of claim 15, wherein potasssium permanganate is used as the oxidant chemical.

17. The method of claim 15, further comprising the step of consolidating said soil after said oxidation thereof.

18. The method of claim 17, comprising the steps of:
   repetitiously sensing the torque load of the cutter drive motor at different elevations of said cutter in said block of soil to obtain an indication of the plasticity of said agitating soil; and
   reversing the direction of rotation of said cutter and consolidating said soil during removal of said cutter from said block of soil when said plasticity readings indicate substantially uniform plasticity of said block of soil.

19. The method of claim 18, comprising the step of sensing the moisture content of said soil and adding a dewatering agent thereto whenever said sensed moisture content is above predetermined levels.

20. The method of claim 19, wherein said dewatering agent is selected from the group consisting of lime, bentonite or a mixture thereof.

* * * * *

(12) REEXAMINATION CERTIFICATE (4635th)
United States Patent
Manchak, Jr.

(10) Number: US 4,834,194 C1
(45) Certificate Issued: Sep. 3, 2002

(54) METHOD AND APPARATUS FOR DETECTION OF VOLATILE SOIL CONTAMINANTS IN SITU

(75) Inventor: Frank Manchak, Jr., 11300 S. Norwalk Blvd., Santa Fe Springs, CA (US) 90670

(73) Assignee: Frank Manchak, Jr., Santa Fe Springs, CA (US)

Reexamination Request:
No. 90/005,548, Nov. 5, 1999

Reexamination Certificate for:
Patent No.: 4,834,194
Issued: May 30, 1989
Appl. No.: 07/120,025
Filed: Nov. 13, 1987

(51) Int. Cl.[7] ........................ E21B 49/00; E21B 47/086
(52) U.S. Cl. ........................ 175/50; 175/17; 175/325.2; 175/393; 175/59; 166/250.01; 166/265; 166/290; 166/366; 166/102; 166/140; 166/147; 166/348; 166/405; 166/128.55; 166/131; 166/263; 166/266

(56) References Cited

U.S. PATENT DOCUMENTS

| | | | |
|---|---|---|---|
| 4,105,253 A | 8/1978 | Showalter | 299/4 |
| 4,332,301 A | 6/1982 | Jonell | 175/50 |
| 4,548,720 A | 10/1985 | Gilligan, III | 252/8.5 B |
| 4,606,675 A | 8/1986 | Mitani et al. | 405/263 |

FOREIGN PATENT DOCUMENTS

WO       8601439       3/1986

*Primary Examiner*—William Neuder

(57) ABSTRACT

The invention relates to methods and apparatus for agitating and heating a sub-surface volume of soil to liberate volatile compositions therefrom which are transmitted through a special flow passage created through the soil to the soil surface where they are analysed to determine the presence or absence of selected contaminants. A low pressure sink is provided to ensure proper flow of volatiles rapidly to the surface and to prevent contamination of adjacent soil blocks or cylinders during treatment.

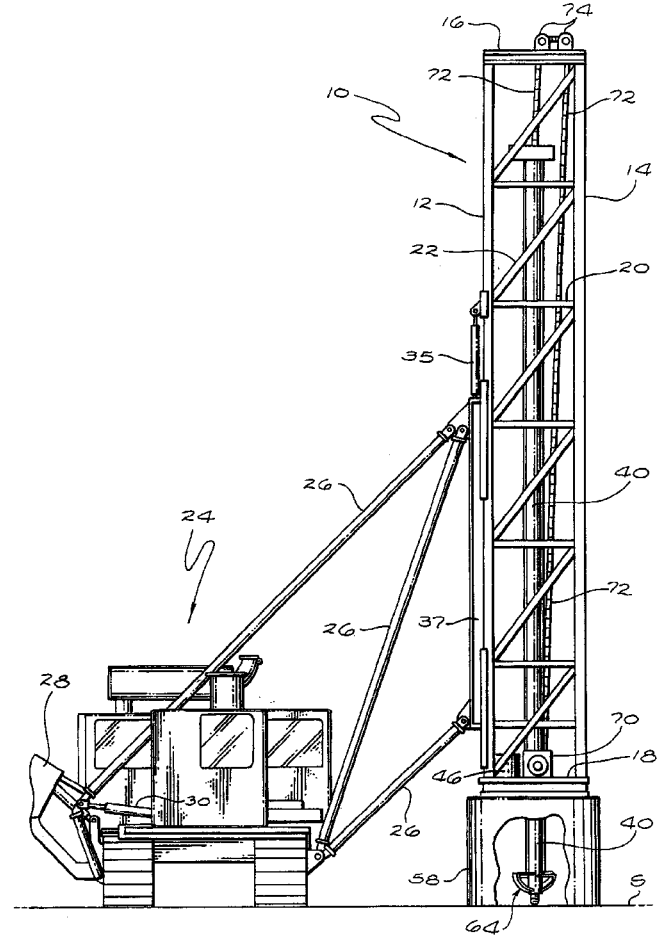

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–20 are cancelled.

\* \* \* \* \*